United States Patent [19]

Metzner et al.

[11] Patent Number: 5,775,329
[45] Date of Patent: Jul. 7, 1998

[54] METHOD AND COMPOUNDS FOR DIAGNOSING CORONARY ARTERY DISEASE

[75] Inventors: Ernest K. Metzner; Mark D. Erion, both of Del Mar, Calif.

[73] Assignee: Gensia, Inc., San Diego, Calif.

[21] Appl. No.: 482,435

[22] Filed: Jun. 7, 1995

[51] Int. Cl.[6] .............................. A61B 5/02; A61B 19/00; C07C 255/08; A61K 31/72

[52] U.S. Cl. .................... 128/695 R; 128/898; 514/597; 552/11; 558/390; 564/361

[58] Field of Search .............................. 514/597; 552/11; 558/390; 564/361; 128/695 R, 898

[56] References Cited

U.S. PATENT DOCUMENTS

| | | | |
|---|---|---|---|
| 3,816,516 | 6/1974 | Cox et al. | 260/501.17 |
| 5,066,678 | 11/1991 | Skidmore et al. | 514/597 |
| 5,088,978 | 2/1992 | Hillman et al. | |
| 5,108,363 | 4/1992 | Tuttle et al. | |
| 5,234,404 | 8/1993 | Tuttle et al. | |
| 5,286,252 | 2/1994 | Tuttle et al. | |
| 5,395,970 | 3/1995 | Tuttle et al. | |

FOREIGN PATENT DOCUMENTS 2 135 678   3/1972   Germany.

OTHER PUBLICATIONS

Young et al., *Drug Dev. Res.* 32:19–28 (1994).
Reitz, et al., *J. Med. Chem.* "Conjugates of Catecholamines. 6. Synthesis and β–Adrenergic Activity of N–(Hydroxyalkyl)catecholamine Derivatives", 28(5):642–647, 1985.

*Primary Examiner*—Johann Richter
*Assistant Examiner*—Ebenezer Sackey
*Attorney, Agent, or Firm*—Lyon & Lyon LLP

[57] ABSTRACT

The present invention relates generally to methods of diagnosis, evaluation and treatment of coronary artery disease in mammals using substituted catecholamines and compounds therefore. It also relates to the preparation, use and administration of these compounds which are useful in the diagnosis, evaluation and treatment of coronary artery disease by means of a feedback controlled drug delivery system that delivers exercise simulating agents which are capable of eliciting acute responses similar to those elicited by aerobic exercise.

20 Claims, 2 Drawing Sheets

METHOD AND COMPOUNDS FOR DIAGNOSING CORONARY ARTERY DISEASE

TECHNICAL FIELD

The present invention relates generally to methods of diagnosis, evaluation and treatment of coronary artery disease in mammals using substituted catecholamines and compounds therefore. It also relates to the preparation, use and administration of these compounds which are useful in the diagnosis, evaluation and treatment of coronary artery disease by means of a feedback controlled drug delivery system that delivers exercise simulating agents which are capable of eliciting acute responses similar to those elicited by aerobic exercise.

BACKGROUND OF THE INVENTION

Exercise stress testing ("EST") is one of the most commonly used tests in the diagnosis of cardiac conditions such as coronary artery disease ("CAD"). Approximately 5 million people in the United States suffer from CAD, resulting in over 1.5 million heart attacks annually, of which 550,000 are fatal. CAD may be diagnosed when the coronary circulation is insufficient to supply the oxygen and nutrient requirements of the heart muscle, resulting in ischemia. Often a cardiac patient has no symptoms at rest and only develops cardiac symptoms under conditions of cardiac stress.

Because of its silent nature and severe consequences, CAD is a diagnostic challenge. Clinical experience has repeatedly confirmed the value of EST in the diagnosis of CAD. However, there are drawbacks that limit its overall use. A significant problem with the procedure is that the level of exercise must be sufficient in order to obtain the greatest sensitivity. In other words, for a test to be considered diagnostically revealing, either the patient must reach a level of stress that causes ischemia, or the patient must complete the protocol by reaching a desired maximal heart rate. A large group of patients in the target group are physically unable to exercise at all, or are unable to achieve a maximal test due to problems such as arthritis, limb abnormalities, obesity, asthma and other conditions.

Other problems are related to the use of this technique, including the fact that exercise stress testing is inconvenient to both patient and doctor. A maximal stress test exhausts most patients and involves a significant recovery time. Additionally, maximal stress tests are potentially risky in that the patient may fall while using the treadmill. Because of the physical movement associated with the exercise, placement of the electrodes is also a problem. Specially designed electrodes which minimize motion artifacts must be securely attached. Taken as a whole, these necessities make EST inconvenient for both the patient and physician. Because of its inherent difficulty, limited sensitivity, limited specificity, and cost, EST is not generally recommended for asymptomatic individuals.

Diagnosis of CAD by methods which can stress the heart in a manner that mimics aerobic activity, while not forcing the patient to engage in strenuous activity would alleviate many of the problems associated with diagnosis of CAD by EST. In fact, a test wherein the heart is stressed without the need for physical exercise would be of great practical utility and would allow for the testing of those individuals who heretofore have been unable to engage in EST.

The present invention relates to the detection of CAD by causing cardiac stress by administration of an exercise simulating agent beta adrenoreceptor agonist (hereinafter ESA) and certain novel compounds useful for CAD detection. The preferred means for detecting CAD during administration of an ESA is by a closed-loop or feedback controlled drug delivery device which controls infusion of the ESA into the blood stream of a patient so that a desired increase in heart rate is obtained. These cardiac responses are monitored by an electrocardiogram. The desired increase in heart rate is achieved by changing the rate of, or stopping, the infusion of the ESA as required.

The closed-loop drug delivery device and certain ESAs useful in this diagnostic system are described in U.S. Pat. No. 5,108,363; in U.S. Pat. No. 5,234,404; in U.S. Pat. No. 5,286,252; and in U.S. Pat. No. 5,395,970, the disclosures of which are incorporated herein by reference.

In use of this diagnostic system it is important that the ESA have a rapid onset of action but even more important that it have a rapid offset so as to closely mimic the stress induced by exercise and to relieve, if necessary, the ischemic state rapidly when the test is completed.

SUMMARY OF THE INVENTION

This invention is directed to novel catecholamine compounds of structural formula I:

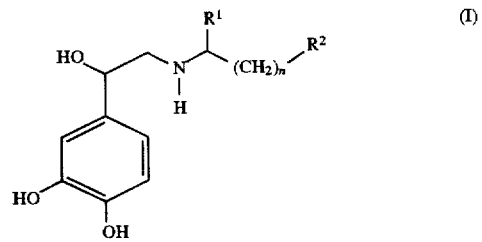

wherein

R$^1$ is —H or lower alkyl of 1 to 3 carbon atoms; R$^2$ is —N$_3$, —CN, —OR$^3$ or —S(O)$_p$R$^3$; R$^3$ is lower alkyl of 1 to 3 carbon atoms; n is an integer from 1 to 5; and p is zero, 1 or 2; and pharmaceutically acceptable salts thereof.

The compounds of the present invention are useful as ESAs with rapid onset and offset of action and are useful in mimicking the cardiovascular response of aerobic activity commonly employed in exercise stress tests when diagnosing CAD.

In another aspect, this invention is directed to a method of eliciting immediate physical responses similar to those elicited by aerobic activity with a relatively quick recovery time which comprises administering to a mammal a compound of this invention or a pharmaceutically acceptable salt thereof by a feedback controlled drug delivery system. This feedback controlled drug delivery system may be open-loop or closed-loop.

According to one aspect of the present invention, there is provided a method of eliciting in a mammal immediate cardiovascular responses similar to those cardiovascular responses elicited by aerobic exercise which comprises: (a) administering an exercise simulating agent (ESA) to said mammal by a closed-loop drug delivery device; (b) controlling infusion of said exercise simulating agent into the bloodstream of said mammal so that a desired range of cardiovascular responses is obtained; (c) monitoring the range of responses of said mammal; and (d) changing infusion of said exercise simulating agent as required to maintain said range of responses. Suitable ESAs include compounds of formula I.

DEFINITIONS

In accordance with the present invention and as used herein, the following terms are defined with the following meanings, unless explicitly stated otherwise.

The term "alkyl" refers to saturated aliphatic groups including straight-chain, branched chain and cyclic groups.

The term "closed-loop" refers to drug delivery systems in which drug is delivered in automatic response to feedback of a physical signal (or response) which could include responses such as heart rate, blood pressure, ECG, cardiac output or other similar physical response.

The term "open loop" refers to drug delivery systems in which drug is delivered at a predetermined rate without any direct or automatic adjustment in response to physiological variables. All adjustments to the delivery rate are made manually after evaluating the feedback data. Such delivery device systems include a syringe pump.

DETAILED DESCRIPTION OF THE INVENTION

Figure 1:
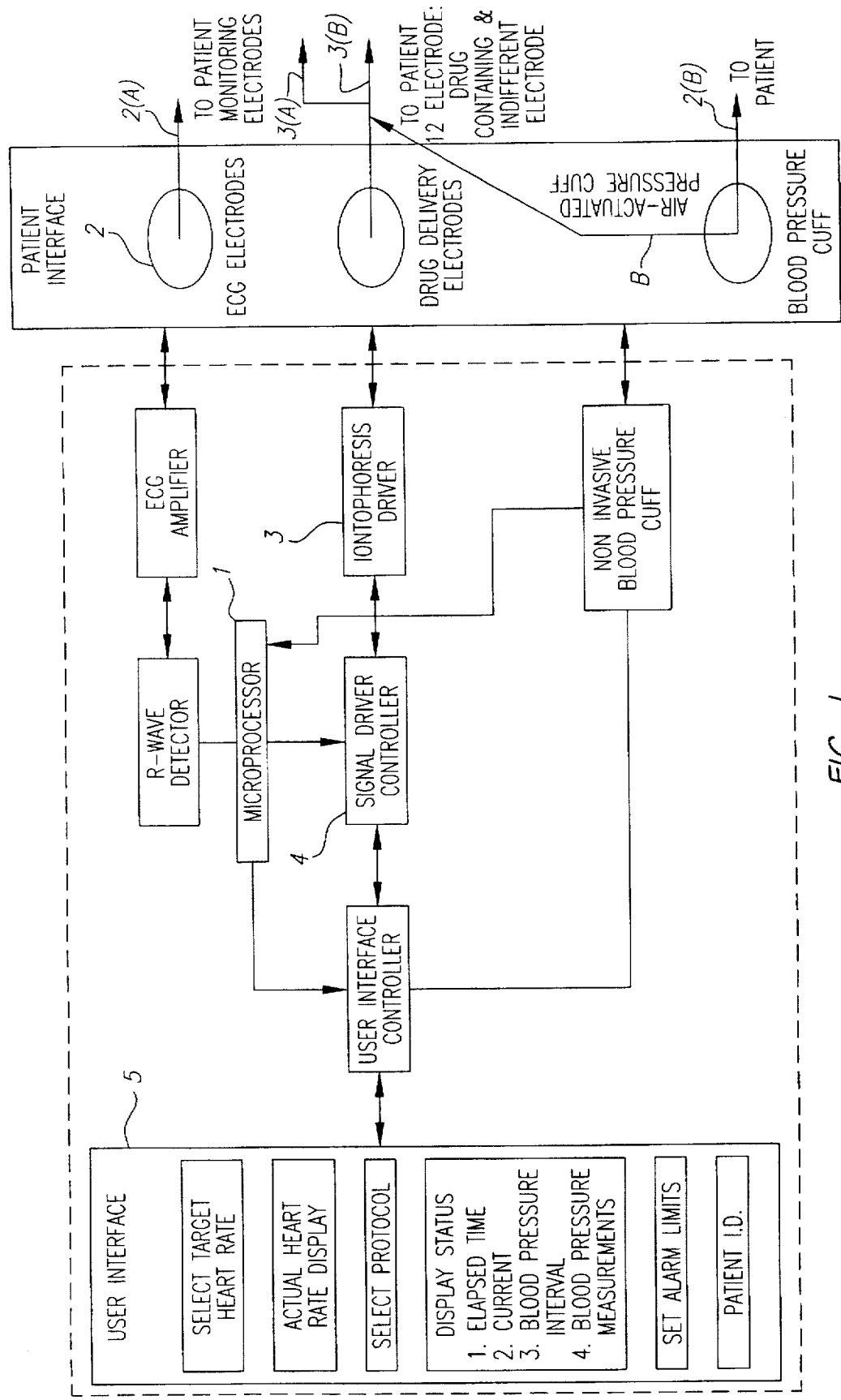
FIG. 1 is a block diagram of a closed-loop transdermal iontophoretic delivery system.

The novel catecholamine compounds of this invention have the following structural formula:

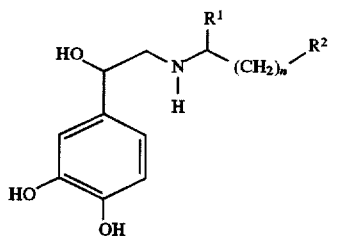

wherein $R^1$ is —H or lower alkyl of 1 to 3 carbon atoms; $R^2$ is —$N_3$, —CN, —$OR^3$ or —$S(O)_pR^3$, wherein $R^3$ is lower alkyl of 1 to 3 carbon atoms; n is an integer from 1 to 5; p is zero, 1 or 2; and include pharmaceutically acceptable salts thereof. Preferred are compounds where $R^2$ is —CN, —$OR^3$ or —$S(O)_pR^3$.

One group of preferred compounds include those wherein $R^2$ is —CN. Also preferred are such compounds where n is 2 or 3. These preferred compounds include:

1-(R)-(3,4-dihydroxyphenyl)-2-(3-cyanopropylamino) ethanol;

1-(R)-(3,4-dihydroxyphenyl)-2-(1-methyl-4-cyanobutylamino)ethanol; and pharmaceutically acceptable salts thereof.

Another group of preferred compounds include those wherein $R^2$ is —$OR^3$. Such preferred ether compounds include those where n is 2 or 3. Also preferred are such compounds where $R^3$ is methyl. These preferred compounds include:

1-(R)-(3,4-dihydroxyphenyl)-2-(3-methoxypropylamino)ethanol;

1-(R)-(3,4-dihydroxyphenyl)-2-(1-methyl-3-methoxypropylamino)ethanol;

1-(R)-(3,4-dihydroxyphenyl)-2-(1-methyl-4-methoxybutylamino)ethanol; and pharmaceutically acceptable salts thereof.

An additional group of preferred compounds include those wherein $R^2$ is —$N_3$. Preferred are such compounds where n is 2 or 3.

A further group of preferred compounds include those wherein $R^2$ is —$S(O)_pR^3$. Such preferred compounds include those where p is 1. Such preferred compounds also include those where $R^1$ is —H. Compounds of this preferred group of compounds include:

1-(R)-(3,4-dihydroxyphenyl)-2-(3-methylsulfinylpropylamino)ethanol; and 1-(R)-(3,4-dihydroxyphenyl)-2-(4-methylsulfinylbutylamino)ethanol; and pharmaceutically acceptable salts thereof.

Particularly preferred are those compounds where $R^2$ is —$S(O)_pR^3$ and p is 0. Such particularly preferred compounds include those where $R^1$ is —H, methyl or ethyl. Preferred are such compounds where $R^3$ is methyl. Also preferred are such compounds where n is 2 or 3. The particularly preferred compounds include:

1-(R)-(3,4-dihydroxyphenyl)-2-(1-methyl-4-methylthiobutylamino)ethanol;

1-(R)-(3,4-dihydroxyphenyl)-2-(4-methylthiobutylamino)ethanol; and 1-(R)-(3,4-dihydroxyphenyl)-2-(3-ethylthiopropylamino) ethanol; and pharmaceutically acceptable salts thereof.

Especially preferred are compounds where p is 0, n is 2, and $R^3$ is methyl. Such compounds include:

1-(R)-(3,4-dihydroxyphenyl)-2-(3-methylthiopropylamino)ethanol; and pharmaceutically acceptable salts thereof.

1-(R)-(3,4-dihydroxyphenyl)-2-(3-methylthiopropylamino)ethanol is the most preferred compound of the present invention.

As may be appreciated from their structural formula, the novel compounds of this invention have at least one asymmetric carbon. This invention is meant to include within its scope all diastereomers, individual enantiomers and mixtures thereof. The preferred compounds are those derived from (R)-norepinephrine. Suitable pharmaceutically acceptable salts include acid addition salts formed from organic or inorganic acids such as hydrochloric, hydrobromic, sulfuric, acetic, citric, oxalic, or tartaric acids and the like. Hydrochloric salts are preferred.

In the method of the present invention precise quantitative amounts of a drug can be delivered to the patient by feedback controlled delivery, preferably by closed-loop delivery. Such a closed-loop delivery system of the present invention may utilize a microprocessor or electronic circuitry to automatically control dosages of an ESA necessary to achieve the same cardiac response between different patients. This system can efficiently and effectively control the effects of the ESA by continuously monitoring the heart rate and blood pressure effects of the ESA via an input device or devices such as an electrocardiograph and blood pressure monitor, processing the information to determine whether to increase or to decrease ESA administration, and then adjusting the amount of ESA delivered, to increase or decrease the heart rate to the desired level. The preferred method of administration is intravenous. Alternatively, a transdermal iontophoretic drug delivery may be used to administer the drug. Such a closed-loop system can safely regulate the amount of ESA delivered to the bloodstream of the patient and, thus, allow a predetermined heart rate to be achieved.

A typical ESA test may include several phases: (a) a pre-ESA monitoring phase; (b) an ESA delivery phase; and (c) a post-ESA monitoring phase. In the pre-ESA monitoring phase, a patient's physical responses are monitored for a period of time prior to beginning administration of the ESA. This phase allows baseline values for physical responses (such as blood pressure and heart rate) to be established and allows the patient to become accustomed to the test equipment. Duration of the pre-ESA monitoring phase is generally about two minutes or longer if additional time is required to establish suitable baseline values. During the ESA delivery phase, ESA is administered to the patient according to the administration protocol selected. Administration protocols include ramp protocols, where the ESA is administered at a rate to give a continuous, basically linear increase in response (such as heart rate) over time or a step protocol where response is increased in discrete increments and then held at that increased level for a period of time before the next incremental increase. The drug delivery phase lasts until a predetermined point is reached, such as maximum recommended heart rate or an elapsed time period; or it may be ended before completion, for example, if physical responses go beyond a preselected range of response or if an arrhythmia occurs. During the post-ESA phase, the patient is monitored until response values approach the baseline value or until a second predetermined response range (such as heart rate below 100) is reached.

The physician may desire a customized testing protocol. For example, the physician may want the patient to maintain a sustained heart rate of 110 for 3 minutes followed by a heart rate of 120 for 2 minutes, in order to create various levels of stress upon the heart. The specific heart rate and corresponding time thereof can be selected by the physician; the software can be programmed to signal the physician when a predetermined maximum heart rate is approaching. Alternatively, the physician may select from a menu any one of several preprogrammed fixed protocols (slow HR rise, moderate HR rise, fast HR rise, etc.) which might be most appropriate for the specific patient. The selected preprogrammed fixed protocol can then be adjusted (if necessary) manually by the physician or automatically by the microprocessor for the desired maximum heart rate.

Additionally, during actual execution of either physician-selected fixed protocols or physician-customized protocols, the system operator may optionally select to HOLD stable at a plateau of a specific HR (not at the maximum heart rate) for a short period of time (potentially several minutes) to enable diagnostic procedures to take place. In this HOLD modality the original protocol is temporarily suspended by the microprocessor and a fixed heart rate maintained (by the closed-loop control of administration of the ESA drug) for the physician's desired time duration. When the HOLD modality is completed (manually indicated by the physician or automatically indicated by the microprocessor) the original protocol may be resumed from the point of suspension or terminated (manually selected by the physician or automatically selected by the microprocessor).

Different patients may require a different dosage of an ESA to achieve the same cardiac response. In addition, if transdermal iontophoretic drug delivery is used, differences in skin resistivity between patients or even different electrode positions on the same patient may also affect the amount of current needed to deliver a given amount of drug iontophorectically. The present closed-loop system automatically compensates for such differences by continuously monitoring the cardiovascular effect of an ESA on a particular patient by way of the sensor, and adjusting the amount of intravenously delivered drug or, alternatively, the current supplied to the iontophoretic delivery device. Therefore the amount of ESA delivered to the patient will be controlled by the feedback data obtained from the patient's physiological changes or from predetermined data entered into the microprocessor by a physician in accordance with the needs of a particular patient.

The ESA test methods of the present invention may be used in conjunction with other diagnostic tools in order to obtain additional information about a patient's cardiovascular condition. For example, use of the ESA test in conjunction with diagnostic tools such as 1) 12-lead ECG to measure ischemia-induced alterations in electrical activity of the heart; 2) echocardiography to measure ischemia-induced wall motion abnormalities; and 3) nuclear scintigraphic imaging to measure ischemia-induced alterations in blood flow distribution to the heart muscle, would expand the usefulness of those techniques. In the past, exercise echocardiography has been impractical due to technical limitations with the equipment involved which were related to the difficulty of monitoring a moving patient with rapidly expanding lungs and tachycardia. Accordingly, due to its ability to simulate the cardiovascular effects of aerobic exercise without bodily motion, use of the test method of the present invention in conjunction with echocardiography may result in a simulated exercise echocardiography which is clinically practical. The ESA test method may also be used in conjunction with radionucleotide imaging using isotopes such as Thallium 201. Since radionucleotide imaging has typically required adequate exercise levels for optimum results, its usefulness for patients unable to exercise adequately or to achieve a maximal heart rate has been severely limited. Use of those techniques in conjunction with the ESA test method will allow application to clinical situations previously considered unsuitable due to the inability of the patient to exercise or achieve maximal heart rate.

Iontophoretic Delivery

Accordingly, in one aspect of the present invention, physiological variables (e.g. heart rate, blood pressure, arrhythmia, ischemia, e.g. ST segment deviation) are monitored in order to determine and automatically regulate the administration of ESA, by means of a closed-loop delivery system consisting of a processor, preferably a microprocessor (which will be described below) and software operatively connected to a physiological monitoring sensor and an iontophoretic delivery device. Such a device comprises a drug delivery electrode which contains the ESA and an indifferent electrode which does not contain the ESA and which functions to complete the electrical circuit and cause delivery of the agonist to the patient.

The drug delivery electrode for the transdermal iontophoretic delivery device may be constructed according to one of various designs which are known in the art. Generally, three types of electrode pads are suitable for use as the drug delivery electrode in the method of the present invention, these being classified as: (1) monolithic pad; (2) reservoir pad; and (3) multilayer pad. Preferred are the monolithic pad and the reservoir pad. See, e.g. U.S. Pat. No. 5,088,978, incorporated herein by reference.

A monolithic electrode pad design provides for including the ESA in a polymer that is attached to the electrode. The polymer can also contain an adhesive to maintain contact with the patient's skin. The ESA is dispersed in the polymer during manufacture; this material is then formed into the pad itself. An example of a class of polymers suitable for use in such a pad are hydrogels. Preferred hydrogels include poly (hydroxy ethyl methacrylate) (HEMA).

A reservoir electrode pad design allows for addition of the ESA drug to an electrode which comprises a disk which is attached to the patient's skin. In such a design, the ESA is contained in a reservoir or cavity in the electrode itself. The reservoir or cavity is formed during the manufacture of the electrode. The ESA can be added in gel form during manufacture of the pad, after its manufacture, or immediately prior to use.

The physiological monitoring sensor and iontophoretic delivery device are attached to a patient as disclosed in FIG. 1. Referring to FIG. 1, the processor (1) provides a signal to the drug delivery device such as by control of current supplied from the signal driver controller (4), and hence the amount of drug delivered to the patient through the transdermal iontophoretic delivery device (3). The amount of drug delivered is a function of patient-specific data programmed into the processor by the physician (indicated generally as user interface (5) in FIG. 1) and the response of the patient to the drug, or as a function of the feedback data obtained from the physiological monitoring sensor (2) as predicated upon the particular needs or physical characteristics of a patient relative to the effect of the ESA upon the patient.

In order to monitor the response of the patient to the ESA and to ensure his safety, in one embodiment as depicted in FIG. 1, an ECG (heart rate) monitoring device (2a) and a blood pressure monitoring device (2b) are provided to monitor the patient's heart rate and blood pressure. These variables may be prominently displayed on a display screen by the microprocessor as depicted in user-interface (5). Additionally, specific parameters, such as the patient's age, height, weight, sex and other necessary data may be programmed into the microprocessor.

As indicated in FIG. 1, an ECG amplifier (6), may be connected to the ECG electrodes, to amplify the signal therefrom, which signal is monitored by an R-wave detector (7), which provides the signal driver controller (4) with information on the heart rate of the patient. If the heart rate or blood pressure go beyond a pre-programmed range, or if arrhythmia develops, the control software may terminate the flow of current to the iontophoretic device which will immediately terminate delivery of the ESA to the patient. Once maximal heart rate is achieved, the flow of drug is also automatically terminated. If ischemia is detected, the drug flow may be manually or automatically terminated.

Figure 2:
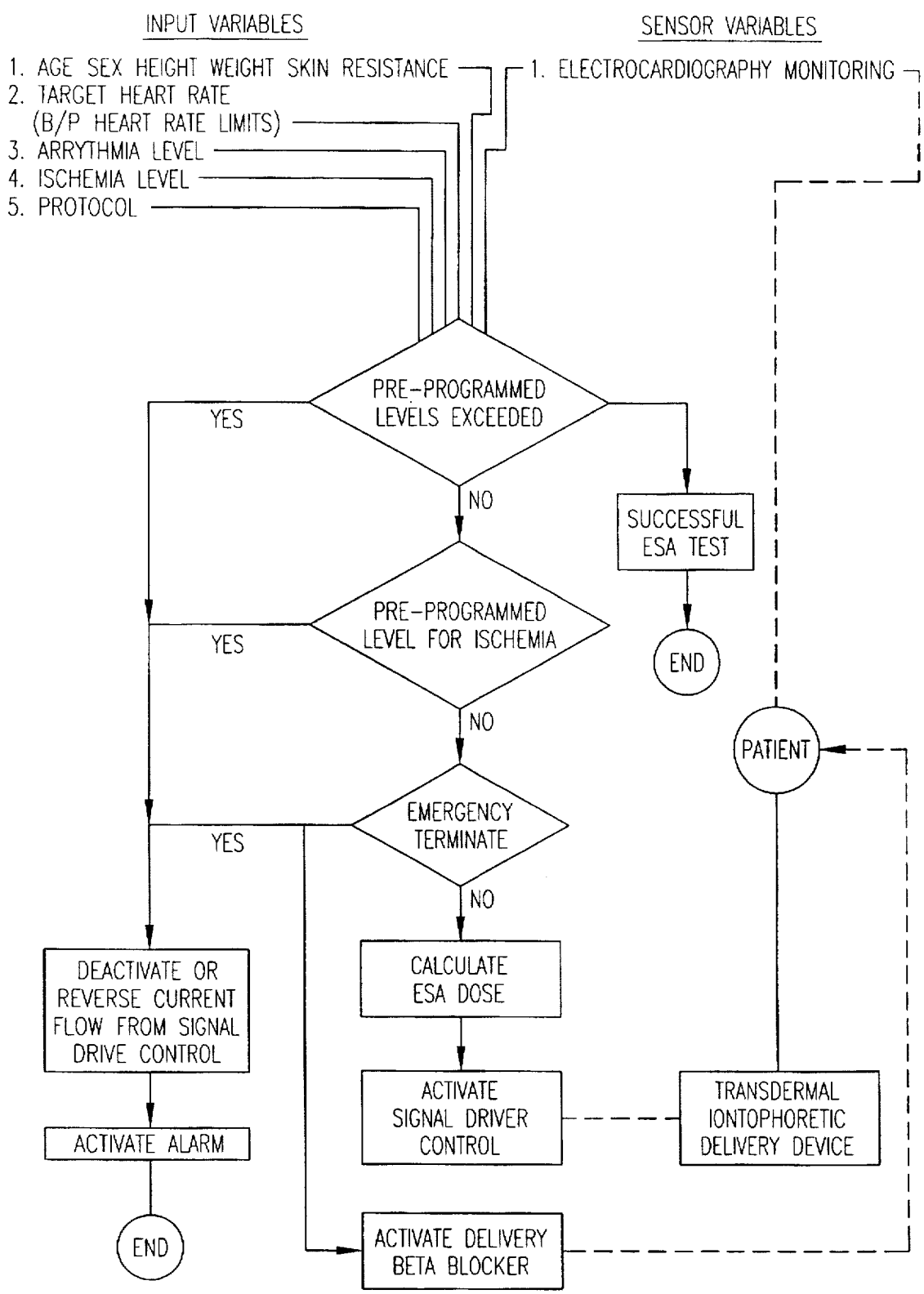
FIG. 2 is a logic diagram for the microprocessor software included in the closed-loop transdermal iontophoretic delivery system.

FIG. 2 depicts a logic diagram for a software program which may be used according to one embodiment of the present invention where iontophoretic drug delivery is employed. Using the input variables and the sensor variables, the current necessary to deliver the ESA to the patient through the iontophoretic device is calculated; or alternatively, these variables can be used to calculate the intravenous infusion rate of the ESA. These variables are monitored and are used in the calculation of the ESA dose and rate of increase or decrease of the ESA dose during the course of the study. Following data entry, the key parameters (e.g. blood pressure, heart rate, impedance, and dose rate) are displayed and alarm signals are set which indicate when a specific pre-set level has been achieved. Software within the microprocessor processes the data obtained from the sensor connected to the patient, and based upon those data—as well as the achievement of a selected target heart rate, or the occurrence of some event wherein the physician or patient desires to terminate the delivery of the ESA—the control software signals the signal driver controller (4) to either increase, decrease, or terminate the administration of ESA.

During the study, the entire electrocardiogram tracing can be recorded; electronic storage media can contain the entire study for a specific patient. The information can also be printed on hard copy by way of a printer attached to the system. Both serve as permanent records for the patient study.

Once the drug delivery begins, such that the ESA begins to affect the patients' heart rate, the blood pressure and heart rate sensors provide the microprocessor and control software with information so that the signal to the iontophoretic device (drug delivery electrode), or alternatively, the rate of the i.v. delivery, may be increased or decreased as required to increase or decrease the amount of drug necessary to obtain the desired response (such as heart rate) in the patient.

Preferred Embodiments

The preferred ESAs used in the methods of the present invention advantageously have half-lives of minimal duration in the bloodstream of a patient. Preferably the ESAs have a half-life in the range of 1 to 5 minutes and more preferably a half-life in the range of 1 to 3 minutes. Optionally, the method of the present invention may further include co-delivery of an antagonist to the ESA, for example, a beta-adrenergic blocker such as propanolol, or esmolol, when quicker reversal of the patient's response to the ESA is desired. Beta-adrenergic blockers may also be administered after the delivery of the ESA is terminated to quickly reverse the ESA's effects. Sublingual administration of nitrates, such as nitroglycerin could also be used to reverse the ESA. However, it is preferred to use a beta-adrenergic blocker. Esmolol is the preferred beta-adrenergic blocker used to reverse the patient's response. The esmolol is preferably administered by i.v. infusion of 50–200 µg/kg/min. If propranolol is used, preferably 1–3 mg is administered by i.v. bolus.

In a preferred embodiment of the present invention, the closed-loop drug delivery device comprises an intravenous ("i.v.") delivery device. Suitable i.v. delivery devices include computer controlled i.v. infusion pumps which may be controlled by a processor, preferably a microprocessor, in much the same manner as are the above-described transdermal iontophoretic delivery devices. Suitable i.v. devices include peristaltic-type, cassette-type, syringe-type, or drop-type apparatus, or any other i.v. fluid delivery device, and includes devices such as those available from Harvard Apparatus or from IVAC Corp.

The novel compounds of the present invention can be administered during the diagnostic procedures described herein by intravenous infusion or by transdermal iontophoresis. However, in the diagnostic method of this invention it is important that the pharmacological effect of the ESA cease as quickly as possible at the predetermined end-point. Unfortunately, transdermal iontophoresis tends to leave a depot of unabsorbed drug under the skin which continues to be delivered to the blood stream after the iontophoresis has been stopped. It is therefore, imperative that the ESA have as short a half-life as possible and hence a short offset time.

Surprisingly, it has been found that the novel compounds of this invention have a short offset time. An example of these novel compounds is 1-(R)-(3,4-dihydroxyphenyl)-2-(3-methylthio-propylamino)ethanol (Compound 11). The oxalate salt of this compound has been shown in dog studies to have a $T_{50}$ (time required for the chronotropic response to decrease by 50%) of 3.6 minutes. This offset time is shorter than for both isoproterenol and arbutamine.

The pharmacodynamic half-life of intravenously administered Compound 11 was estimated and compared with isoproterenol and arbutamine, from the decline in stable heart rate achieved at the highest dose (100 ng/kg/min). The results shown in Table I, show that Compound 11 exhibits a substantially shorter $T_{50}$ than isoproterenol and arbutamine despite similar increases in heart rate.

TABLE I

Pharmacodynamic offset times after I.V. administration

| Compound | Δ Heart Rate (beats/min) | $T_{50}$ (min) |
|---|---|---|
| 11 | 109 ± 4 | 3.6 ± 0.3 |
| Isoproterenol | 103 ± 12 | 5.5 ± 1.0 |
| Arbutamine | 84 ± 9 | 7.2 ± 1.1 |

The Δ Heart Rate represents the stable levels expressed as the increase over baseline heart rate achieved at the highest dose (100 ng/kg/min) of each compound after administration of ascending doses. The $T_{50}$s were measured from end of infusion.

Formulations

Compounds of the invention are administered to the patient at the dose of from 0.1 to 10 μg/kg/min of body weight, preferably 0.1 μg/kg/min to 4 μg/kg/min of body weight for a human being. An important aspect of this invention is that compounds of the present invention are preferably administered intravenously, but they also may be given iontophorectically.

For i.v. administration, the pharmaceutical compositions of the invention may be in the form of a sterile injectable preparation, such as a sterile injectable aqueous or oleaginous suspension. This suspension may be formulated according to the known art using suitable dispersing or wetting agents and suspending agents. Suitable dispersing or wetting agents include naturally occurring phosphatide (e.g. lecithin), a condensation product of an alkylene oxide with a fatty acid (e.g. polyoxyethylene stearate), a condensation product of ethylene oxide with a long chain aliphatic alcohol (e.g. heptadecaethyleneoxycetanol), a condensation product of ethylene oxide with a partial ester derived from a fatty acid and a hexitol anhydride (e.g. polyoxyethylene sorbitan monooleate). Suitable suspending agents include sodium carboxymethylcellulose, methylcellulose, hydroxypropyl methylcellulose, sodium alginate, polyvinylpyrrolidone, gum tragacanth and gum acacia. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of an injectable.

Formulations suitable for parenteral administration include aqueous and non-aqueous isotonic sterile injection solutions which may contain antioxidants, chelators, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Further, compounds and methods of the present invention may be administered transdermally, for example as described by Richard Baker in "Controlled Release of Biologically Active Agents," John Wiley & Sons, New York. 1987. For iontophoretic transdermal administration, the ESA is formulated in a polymer or a liquid reservoir system containing drug solutions similar to those used in a parenteral formulation. Suitable polymers include hydrogels. Preferred hydrogels include poly (hydroxyethylmethacrylate) (referred to as HEMA). The hydrogel may comprise poly(HEMA) [Benz Research], hydroxypropylmethyl cellulose Methocel, EIOM, [Dow Chemical], Hypol (W. R. Grace & Co.) or Carbopol [934P, BF Goodrich] and may include a preservative to prevent microbial growth; parabens, such as methyl, ethyl and propyl are preferred preservatives. Small amounts of EDTA as a chelating agent may be included. Preferred gels also include an antioxidant to prevent oxidation due to drug-electrode interaction. Preferred antioxidants include bisulfite and vitamin C. The solvent for the gel may comprise deionized, pyrogen-free water, propylene glycol, or polyethylene glycol (PEG 400, 10–20%). If desired, ethanol (100%) may be added as a cosolvent. The concentration of the drug within the gel is preferably in the range of approximately 5–25 mg/ml gel. It may be desirable to add a small amount of buffer (e.g. citrate, phosphate buffer) to maintain the pH in the electrode.

Preparation of Compounds of the Present Invention

The process used to prepare the compounds of this invention is illustrated by the following reaction scheme:

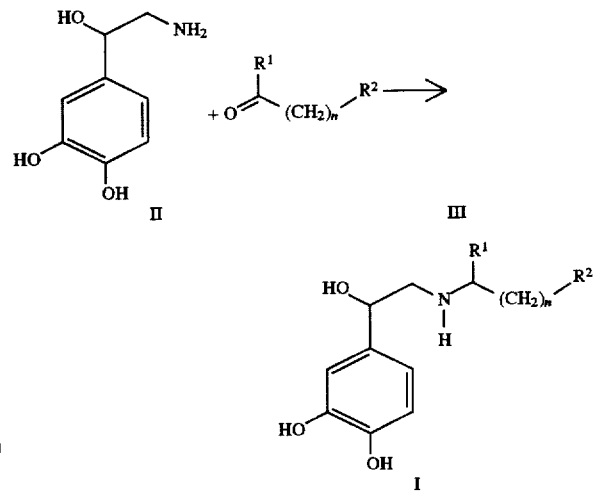

It comprises the reductive alkylation of (R)-norepinephrine with an aldehyde or ketone of structural formula:

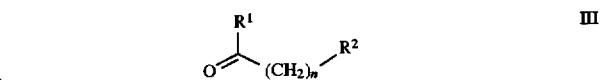

wherein $R^1$, $R^2$ and n are as defined previously in connection with formula I. The alkylation is conducted in a mixture of an alkanol of 1 to 3 carbon atoms, preferably methanol and an alkanoic acid of 2 to 3 carbon atoms, preferably acetic acid.

The temperature at which the reaction is performed is not critical since it will conveniently proceed at any temperature from about 0° C. to about 60° C. However, room temperature, (15°–25° C.) may be most convenient. At this temperature the reaction is completed in about 15 to 20 hours.

The reducing agent can be either hydrogen gas in the presence of a noble metal catalyst such as platinum or palladium on carbon or a metal hydride complex such as sodium cyanoborohydride depending to some extent on the nature of the functional groups present.

Method A. Hydrogenation

To a solution of (R)-(–)-norepinephrine (0.42 g, 2.5 mmol) in 35 mL of methanol containing 0.35 mL of acetic acid was added 2.5 to 5 mmol of the desired aldehyde or ketone. The solution was purged with argon gas and 100 mg of 10% platinum on carbon was added. The resulting mixture was stirred under an atmosphere of hydrogen for 18 hours. The reaction mixture was filtered to remove the catalyst and concentrated under vacuum to approximately 5 mL. The crude product was purified by silica gel chromatography using dichloromethane/methanol/acetic acid (10:3:1). The fractions containing the desired product as determined by TLC in the same system were pooled and concentrated to dryness. The resulting acetate salts were converted to the oxalate salts by treatment with oxalic acid in ethanol followed by addition of diethyl ether to precipitate the desired oxalate salt.

Method B. Hydride Reduction

To a mixture of (R)-(–)-norepinephrine (1.0 g, 6 mmol) and 6 to 10 mmol of the desired aldehyde or ketone in a mixture of 30 mL of methanol containing 0.6 mL of acetic acid was added sodium cyanoborohydride (384 mg, 6 mmol). The reaction mixture was stirred for 18 hours and evaporated to dryness under vacuum. The residue was dissolved in 20 mL of ethanol, filtered to remove any insolubles and further purified by silica gel chromatography using dichloromethane/methanol/acetic acid (10:3:1). Fractions containing the desired product as determined by TLC in the same system were pooled and concentrated to dryness. The resulting acetate salts were converted to the oxalate salts by treatment with oxalic acid in ethanol followed by addition of diethyl ethyl ether to precipitate the desired oxalate salt.

The compounds of this invention and their preparation can be understood further by the examples which illustrate the utility of the compounds of the present invention and some of the processes by which these compounds are prepared. These examples should not however be construed as specifically limiting the invention and variations of the invention, now known or later developed, are considered to fall within the scope of the present invention as herein after claimed.

EXAMPLE 1

Preparation of 1-(R)-(3,4-dihydroxyphenyl)-2(3-cyanopropylamino)ethanol oxalate salt Step A: Preparation of 3-cyanopropanal A mixture of 2-(2-bromoethyl)-1,3-dioxolane (8.14 g, 45 mmol), potassium cyanide (5.85 g, 90 mmol), and 18-crown-6 (30 mg) in 30 mL of dimethylformamide was stirred for 72 hours at 23° C. The reaction mixture was filtered, diluted with 70 mL of dichloromethane and washed twice with 10 mL of water. The organic phase was dried over magnesium sulfate and distilled under vacuum to yield 3.2 g of 2-(2-cyanoethyl)-1,3-dioxolane. This was stirred in 20 mL of 1M HCl for 40 hours. The mixture was neutralized with sodium bicarbonate and extracted with 100 mL of dichloromethane. The dichloromethane extract was dried over magnesium sulfate and evaporated to yield 2.5 g of the desired aldehyde as an oil.

Step B: Preparation of 1-(R)-(3,4-dihydroxyphenyl)-2-(3-cyanopropylamino)ethanol oxalate salt Following the procedure substantially as described in General Method A, (R)-norepinephrine was reacted with the aldehyde, 3-cyano-propanal, from Step A to give the title compound as a white solid.

Calc. for $C_{14}H_{18}N_2O_7$: (%) C-51.53, H-5.56, N-8.58. Found: (%) C-51.50, H-5.67, N-8.61. m.p. 150°–154° C.

EXAMPLE 2

Preparation of 1-(R)-(3,4-dihydroxyphenyl)-2(1-methyl-4-cyanobutylamino)ethanol oxalate salt Step A: Preparation of 5-cyano-2-pentanone 5-Chloro-2-pentanone ethylene ketal (13.2 g, 80 mmol) was heated in a mixture of 14 g of potassium cyanide, 100 mg of 18-crown-6 and 80 mL of dimethylformamide at 50° C. for 48 hours. The mixture was filtered and evaporated to dryness. The product was extracted into dichloromethane, washed with water and further purified by silica gel chromatography using hexane/ethyl acetate (4:1). The resulting 5-cyano-2-pentanone ethylene ketal (7 g) was stirred in 16 mL of 85% formic acid for 24 hours. The reaction mixture was neutralized with sodium bicarbonate and extracted with diethyl ether. The ether extract was dried over magnesium sulfate and evaporated to yield 4 g of the desired ketone as an oil.

Step B: Preparation of 1-(R)-(3,4-dihydroxynhenyl)-2-(1-methyl-4-cyanobutylamino)ethanol oxalate salt Following the procedure substantially as described in Method A Hydrogenation, (R)-norepinephrine was condensed with the ketone from Step A to produce a white solid.

TLC (silica gel; methylene chloride: methanol: acetic acid 10:2:1) Rf=0.3;

1H NMR (DMSO-$d_6$) δ 6.7 (m, 3H, ArH), 4.55 (d, 1H, CHOH), 2.6–3.0 (m, 3 H, $CH_2NCH$), 2.5(m, 2H, $CH_2CN$), 1.4–1.7(m, 4H, $CH_2CH_2$), 1.1(d, 3H, $CH_3$).

EXAMPLE 3

Preparation of 1-(R)-(3,4-dihydroxyphenyl)-2(3-methoxypropylamino)ethanol oxalate salt Step A: Preparation of 3-methoxypropanol 5 g of 1,1,3-trimethoxypropane (Aldrich Chemical Company) was stirred in 10 mL of 60% trifluoroacetic acid for 18 h at room temperature. The mixture was neutralized with sodium bicarbonate and extracted with 50 mL of ether. The ether extract was washed with water and dried over magnesium sulfate. Evaporation of the ether yielded 3.2 grams of the desired aldehyde as an oil.

Step B: Preparation of 1-(R)-(3,4-dihydroxynhenyl)-2-(3-methoxy-propylamino)ethanol oxalate salt Following the procedure substantially as described in Method A Hydrogenation, (R)-norepinephrine was condensed with the 3-methoxypropanal from Step A to give the title compound.

TLC (silica gel; methylene chloride: methanol: acetic acid 10:2:1) Rf=0.4; Calc. for $C_{14}H_{21}NO_8 \cdot H_2O$: (%) C-48.14, H-6.63, N-4.01. Found: (%) C-48.39, H-6.61, N-4.00.

EXAMPLE 4

Preparation of 1-(R)-(3,4-dihydroxyphenyl)-2(1-methyl-3-methoxy-propylamino)ethanol oxalate salt Step A: Preparation of 4-methoxy-2-butanone 5 g (33.7 mmol) of 1,3,3-trimethoxybutane (Aldrich Chemical Company) was stirred in 8 mL of 75% formic acid for 18 h at room temperature. The mixture was neutralized with sodium bicarbonate and extracted with 75 mL of ether. The ether extract was dried over magnesium sulfate and evaporated to yield 2.3 g of the desired ketone as an oil.

Step B: Preparation of 1-(R)-(3,4-dihydroxyphenyl)-2-(1methyl-3-methoxypropylamino)ethanol oxalate salt Following the procedure substantially as described in Method A Hydrogenation, (R)-norepinephrine was condensed with the ketone from Step A to give the title compound as a white solid.

TLC (silica gel; methylene chloride: methanol: acetic acid 10:2:1) Rf=0.6; Calc. for $C_{15}H23NO8$: (%) C-52.17, H-6.71, N-4.06. Found: (%) C-51.92, H-6.80, N-4.06.

EXAMPLE 5

Preparation of 1-(R)-(3,4-dihydroxynhenyl)-2(1methyl-4-methoxy-butylamino)ethanol oxalate salt Step A: Preparation of 5-methoxy-2-pentanone To a solution of sodium methoxide prepared by the addition of 0.8 g of sodium to 35 mL of methanol was added 5-chloro-2-pentanone ethylene ketal (3 g, 180 mmol). The mixture was heated in a steel bomb at 100° C. for 18 hours. The methanol was removed by evaporation under reduced pressure and the residue was extracted into 20 mL of ether. The ether extract was washed with water, saturated saline solution and dried over magnesium sulfate. Evaporation of the ether yielded 1.6 grams of 5-methoxy-2-pentanone ethylene ketal. This was stirred in 10 mL of 75% formic acid for 24 h at room temperature. The mixture was neutralized with sodium bicarbonate and extracted with 50 mL of ether. The ether extract was washed with water, saturated saline solution and dried over magnesium sulfate. Evaporation yielded 1.2 g of the desired ketone as an oil. Step B: Preparation of 1-(R)-(3,4-dihydroxyphenyl)-2-(1-methyl-4methoxybutylamino)ethanol oxalate salt Following the procedure substantially as described in Method A Hydrogenation, (R)-norepinephrine was condensed with 5-methoxy-2-pentanone from Step A to give the title compound.

TLC (silica gel; methylene chloride: methanol: acetic acid 10:2:1) Rf=0.5; Calc. for $C_{16}H_{25}NO8$: (%) C-53.48, H-7.01, N-3.90. Found: (%) C-51.99, H-6.98, N-3.76.

EXAMPLE 6

Preparation of 1-(R)-(3,4-dihydroxyphenyl)-2-(3methylsulfinylpropylamino) ethanol oxalate salt To a solution of 230 mg of 1-(R)-(3,4-dihydroxyphenyl) -2-(3-methylthiopropylamino)ethanol oxalate (product of Example 11) in 2 mL of water was added 100 µL of 30% hydrogen peroxide. The solution was stirred for 20 minutes at room temperature and evaporated to dryness under vacuum. The residue was evaporated twice from 5 mL of ethanol to remove any remaining water and then stirred in 15 mL of ether to yield 150 mg of the desired compound as a white solid.

TLC (silica gel; n-butanol: acetic acid: water 4:1:1) Rf=0.1; Calc. for $C_{14}H_{25}NO_{10}S$ (dihydrate): (%) C-42.10, H-6.31, N-3.51. Found: (%) C-42.31, H-5.89, N-3.26.

EXAMPLE 7

Preparation of 1-(R)-(3,4-dihydroxyphenyl)-2-(4methylsulfinylbutylamino) ethanol oxalate salt To a solution of 45 mg of 1-(R)-(3,4-dihydroxyphenyl)-2-(4-methylthiobutylamino)ethanol oxalate salt (product of Example 9) in 2 mL of water was added 14 µL of 30% hydrogen peroxide. The solution was stirred for 20 minutes at room temperature and evaporated to dryness under vacuum. The residue was evaporated twice from 3 mL of ethanol to remove any remaining water and then stirred in 10 mL of ether to yield 21 mg of the desired compound as a white solid.

TLC (silica gel; n-butanol: acetic acid: water 4:1:1) Rf=0.1;

1H NMR (DMSO-$d_6$) δ 6.7 (m, 3H, ArH), 4.70 (d, 1H, CHOH), 2.95 (m, 4H, $CH_2NCH_2$), 2.70(m, 2H, $CH_2S$), 2.5 (S, 3H, $CH_3S$), 1.7(m, 4H, $CH_2CH_2$).

EXAMPLE 8

Preparation of 1-(R)-(3,4-dihydroxyphenyl)-2(1methyl-4-methylthiobutylamino)ethanol oxalate salt
Step A: Preparation of 5-methylthio-2-pentanone To a solution of sodium methoxide prepared by slowly adding 2.4 g (54 mmol) of sodium to 40 mL of methanol was added 4.8 g (48 mmol) of methylmercaptan followed by 6.6 g (40 mmol) of 5-chloro-2-pentanone ethylene ketal. The mixture was refluxed for 4 h and an additional 50 mmol each of sodium and methylmercaptan was added and then refluxed an additional 4 hours to complete the reaction. 50 mL of toluene was added and the mixture washed twice with 10 mL of 1N sodium hydroxide. The toluene layer was dried over magnesium sulfate and evaporated to give 7.1 g of 5-methylthio-2-pentanone ethylene ketal. This was stirred in 60 mL of 70% trifluoroacetic acid for 24 h at room temperature. The mixture was neutralized with sodium carbonate and extracted with 200 mL of ether. The ether extract was dried and evaporated to yield 3.5 g of the desired ketone as an oil.

Step B: Preparation of 1-(R)-(3,4-dihydroxyphenyl)-2-(1methyl-4-methylthiobutylamino)ethanol oxalate salt Following the procedure substantially as described in Method B Hydride Reduction, (R)-norepinephrine was condensed with 5-methylthio-2-pentanone from Step A to give the title compound as a white solid.

TLC (silica gel; methylene chloride: methanol: acetic acid 10:2:1) Rf=0.19;

1H NMR (DMSO-$d_6$) δ 6.7 (m, 3H, ArH), 4.70 (d, 1H, CHOH), 3.05 (m, 3H, $CH_2NCH$), 2.45(m, 2H, $CH_2S$), 2.05 (S, 3H, $CH_3S$), 1.6(m, 4H, $CH_2CH_2$), 1.20 (S, 3H, $CH_3S$).

EXAMPLE 9

Preparation of 1-(R)-(3,4-dihydroxyphenyl)-2-(4methylthiobutylamino)ethanol oxalate salt Step A: Preparation of 4-(methylthio)butanal To a sodium methoxide solution prepared by slow addition of 4.8 g of sodium to 70 mL of methanol was added 10 g (0.2 mol) of methylmercaptan followed by 10 g (67.5 mmol) of 4-bromobutyronitrile (Aldrich Chemical Company). The mixture was stirred for 18 hours, filtered and evaporated under vacuum to remove methanol. The residue was extracted with 100 mL of toluene and the toluene extract washed with water, saturated sodium bicarbonate and dried over magnesium sulfate. Removal of the toluene by distillation yielded 7 g of 4-(methylthio)butyronitrile. This nitrile was dissolved in 25 mL of toluene and cooled under argon to 3° C. 55 mL of 1.5M diisobutylaluminum hydride in toluene was added dropwise over 1.5 h. The mixture was stirred for 15 minutes and then adjusted to pH=2 with 6N hydrochloric acid. 20 mL of toluene was added and the toluene phase separated, washed with 1N hydrochloric acid,

15 then water and dried over magnesium sulfate. Evaporation of the toluene yielded 3.2 g of the desired aldehyde as an oil.

Step B: Preparation of 1-(R)-(3,4-dihydroxyphenyl)-2-(4-methyl-thiobutylamino) ethanol oxalate salt Following the procedure substantially as described in Method B Hydride Reduction, (R)-norepinephrine was condensed with 4-(methylthio)butanal from Step A to give the title compound as a white solid.

TLC (silica gel; methylene chloride: methanol: acetic acid 10:2:1) Rf=0.5; Calc. for $C_{15}H_{23}NO_7S.0.5\ H_2O$: (%) C-48.64, H-6.53, N3.78. Found: (%) C-48.90, H-6.50, N-3.78. 1H NMR (DMSO-$d_6$) δ 6.7 (m, 3 H, ArH), 4.70 (d, 1H, CHOH), 2.95 (m, 4H, $CH_2NCH_2$), 2.45(t, 2H, $CH_2S$), 2.1 (S, 3H, $CH_3S$), 1.60(m, 4H, $CH_2CH_2$).

EXAMPLE 10

Preparation of 1-(R)-(3,4-dihydroxyphenyl)-2-(3-ethylthioproylamino)ethanol oxalate salt Step A: Preparation of 3-ethylthiopropanal A mixture 10 mL of ethylmercaptan and 2 drops of triethylamine was cooled to 3° C. under argon. Acrolein (2 mL) was added dropwise over 2 h. The mixture was stirred for 2 h then allowed to warm to room temperature. Excess ethylmercaptan was removed by vacuum distillation and the residue further purified by silica gel chromatography using hexane/ethyl acetate (3:1) to yield 0.73 g of the desired aldehyde as an oil.

Step B: Preparation of 1-(R)-(3,4-dihydroxyphenyl)-2-(3-ethylthioproylamino)ethanol oxalate salt Following the procedure substantially as described in Method B Hydride Reduction, (R)-norepinephrine was condensed with 3-(ethylthio)propionaldehyde to give the title compound as a white solid.

TLC (silica gel; methylene chloride: methanol: acetic acid 10:3:1) Rf=0.5; Calc. for $C_{15}H_{23}NO_7S.0.5\ H_2O$: (%) C-48.64, H-6.53, N-3.78. Found: (%) C-48.80, H-6.54, N-3.73.

EXAMPLE 11

Preparation of 1-(R)-(3,4-dihydroxyphenyl)-2-(3-methylthioproylamino)ethanol oxalate salt Following the procedure substantially as described in Method B Hydride Reduction, sodium cyanoborohydride (0.38 g, 6 mmol) was added to a mixture of (R)norepinephrine (1 g, 6 mmol), 3-(methylthio) propionaldehyde (0.9 g, 8.7 mmol) and acetic acid (0.6 mL) in methanol (30 mL). After overnight stirring, the reaction mixture was evaporated to dryness. The residue was dissolved in ethanol, filtered, and chromatographed over silica gel using dichloromethane/methanol/acetic acid as elutant. Fractions containing the desired product were pooled and evaporated to dryness. The residue was dissolved in ethanol (5 mL), filtered, and evaporated to dryness to yield 1.2 g of the acetate salt. The acetate salt was dissolved in ethanol (8 mL) and oxalic acid (170 mg) was added. Diethyl ether was added and the product oxalate salt was collected by filtration as a white solid, yield 855 mg (41%).

TLC (silica gel; methylene chloride: methanol: acetic acid 10:2:1) Rf=0.35; Calc. for $C_{14}H_{21}NO_7S$: (%) C-48.41, H-6.09, N-4.03. Found: (%) C-48.41, H-6.39, N-3.81.

m.p. 105°–107° C.

EXAMPLE 12

Preparation of 1-(R)-(3,4-dihydroxyphenyl)-2-(1-methyl-4-azidobutylamino)ethanol oxalate salt Step A: Preparation of 5-azidopentan-2-one 5-Chloro-2-pentanone ethylene ketal (5.0 g, 30.4 mmol) was stirred in DMF with lithium azide (5.95 g, 120 mmol) at 60° C. for 48 hrs. The mixture was evaporated to dryness. The product was then dissolved in toluene (50 ml) and washed with water (3×15 ml). The organic phase was evaporated and the resulting 5-azido-2-pentanone ethylene ketal was stirred in 50 ml of 70% trifluoroacetic acid for 24 hrs. The reaction mixture was neutralized with sodium bicarbonate and extracted with ethyl acetate. The organic phase was dried over magnesium sulfate and evaporated to yield the desired ketone as an oil.

Step B: Preparation of 1-(R)-(3,4-dihydroxyphenyl)-2-(1-methyl-4-azidobutylamino)ethanol oxalate salt Following the procedure substantially as described in Method B Hydride Reduction, (R)-norepinephrine was condensed with 5-azidopentan-2-one from Step A to give the title compound in 15% yield.

TLC (silica gel; n-butanol:acetic acid:water 4:1:1) Rf=0.7

1H NMR (DMSO-$d_6$) δ 1.1 (d, 3H, $CH_3$—CH), 1.3–1.6 (m, 4H, CH—$CH_2$—$CH_2$—$CH_2$), 2.6–2.7 (m, 2H, CH—$CH_2$—NH), 2.7–2.8 (m, 1H, HN—CH—$CH_3$), 3.35 (t, 2H, $CH_2$—$CH_2$—$N_3$), 4.5 (t, 1H, HO—CH—$CH_2$), 6.5–6.8 (m, 3, Ar—H). Calc. for $C_{15}H_{22}N_4O_7$: (%) C-48.65, H-5.99, N-15.13. Found: (%) C-49.15, H-6.14, N-14.80.

The compounds in the following table were prepared using the methods described above.

| -R$^1$ | -R$^2$ | n | -R$^3$ | p |
|---|---|---|---|---|
| $CH_3$ | CN | 3 | — | — |
| $CH_3$ | OR$^3$ | 2 | $CH_3$ | — |
| H | OR$^3$ | 2 | $CH_3$ | — |
| $CH_3$ | OR$^3$ | 3 | $CH_3$ | — |
| H | CN | 2 | — | — |
| $CH_3$ | S(O)pR$^3$ | 3 | $CH_3$ | 0 |
| $CH_3$ | $N_3$ | 3 | — | — |
| H | $N_3$ | 2 | — | — |
| $CH_3$ | S(O)pR$^3$ | 3 | $CH_3$ | 1 |
| H | CN | 1 | — | — |
| H | S(O)pR$^3$ | 2 | $CH_3$ | 0 |
| H | S(O)pR$^3$ | 3 | $CH_3$ | 0 |
| H | S(O)pR$^3$ | 2 | $CH_2CH_3$ | 0 |
| H | S(O)pR$^3$ | 2 | $CH_3$ | 1 |
| H | S(O)pR$^3$ | 3 | $CH_3$ | 1 |

EXAMPLE 13

Pharmacodynamics in conscious dogs during i.v. administration

Dogs were trained to lie quietly on a table. Novel catecholamine compounds were administered via a venous catheter acutely placed in a leg vein. Each compound was given in a stepwise, ascending dose protocol (1, 3, 10, 30, 100 ng/kg/min i.v.) with each dose infused for 10 minutes. Heart rate was recorded by computer from ECG limb leads at 5 second intervals throughout the experiment. $T_{50}$ for heart rate decline was measured from termination of infusion (100 ng/kg/min i.v.) to 50% fall in heart rate towards baseline.

| Example # | T$_{50}$ (min) | Δ Heart rate |
|---|---|---|
| 1 | 6.9 ± 0.6 | 109 ± 5 |
| 4 | 5.0 ± 0.7 | 98 ± 8 |
| 6 | 5.4 ± 1.3 | 93 ± 3 |
| 9* | 3.6 ± 0.34 | 93 ± 6 |
| 11 | 3.6 ± 0.2 | 109 ± 4 |

*The dose for compound 9 reached 300 ng/kg/min.

EXAMPLE 14

Pharmacodynamics in conscious dogs during transdermal iontophoretic administration Dogs were trained to lie quietly on a table. Heart rate was monitored by ECG limb leads. Novel catecholamines were administered from a gel-filled electrode placed on the surface of the skin. A second electrode was placed on the skin to complete the electrical circuit. All compounds were delivered using a current of 0.25 mA for a period of 10 minutes. Heart rate was monitored by the ECG, and the T$_{50}$ of the compound was measured as the time after termination of current required for heart rate to return 50% toward baseline rate. A "delay" time was also measured as the time required for heart rate to begin to fall, following termination of current. Results are summarized in the following table.

| Example # | Concentration (mM) | Delay (min) | T$_{50}$ (min) | Δ Heart Rate (beats/min) |
|---|---|---|---|---|
| Isoproterenol | 2.5 | 1.2 ± 0.5 | 12.2 ± 1.9 | 80 ± 11 |
| Arbutamine | 20 | 2.3 ± 1.4 | 24.8 ± 2.7 | 84 ± 5 |
| Ex 4 | 2 | 0.3 ± 0.1 | 9.1 ± 0.8 | 79 ± 8 |
| Ex 1 | 3 | 1.9 ± 0.5 | 12.4 ± 1.3 | 77 ± 1.3 |
| Ex 11 | 12 | 0.8 ± 0.2 | 12.7 ± 3.6 | 89 ± 7 |
| Ex 9 | 8 | 0.6 ± 0.6 | 9.3 ± 0.5 | 82 ± 9 |
| Ex 6 | 8 | 0.9 ± 0.5 | 13.6 ± 2.3 | 93 ± 6 |

Example 15

In Vitro Bioassays for $\beta_1$-, $\beta_2$- and α-Adrenoreceptor Activity

Functional evaluation of $\beta_1$-, $\beta_2$- and α-adrenoreceptor activity was performed using in vitro preparations of guinea pig atria, guinea pig trachea, and rabbit aorta, respectively (Young, et. al. *Drug Dev. Res.* 1994, 32, 19–28).

For the atrial assay of $\beta_1$-adrenergic activity, male Hartley guinea pigs (350–500 g; Charles River Laboratories, Wilmington, Mass.) were sacrificed by decapitation and the hearts were excised and placed in ice-cold oxygenated Krebs Ringer buffer. The atria were separated from the ventricles, leaving the right and left atria attached as a pair. A suture was placed at the apex of each atrial appendage for securing the tissue within the organ bath. The water-jacketed 25-ml organ baths were maintained at 37° C. and filled with Krebs Ringer solution aerated with 95% O$_2$ and 5% CO$_2$. The atrial pairs were equilibrated for at least 20 min after application of 1 g resting tension. $\beta_1$-adrenergic activity was assessed using atrial rate (beats per min) and amplitude of contraction (g tension) which were monitored at 1 and 5 min after dosing. Concentration-response curves ($10^{-11}$–$10^{-4}$M) were obtained by cumulative addition of drug to the bath. Following the completion of the dose response curves, isoproterenol was added to assess maximal response of each atrial preparation. EC$_{50}$ values were calculated from the rate results of approximately four atrial preparations per compound.

For the tracheal assay of $\beta_2$-adrenergic activity, male Hartley guinea pigs (350–500 g) were sacrificed by carbon dioxide inhalation and the trachea was gently excised and placed in ice-cold aerated Krebs Ringer solution. $\beta_2$-adrenergic activity was assessed as the relaxation of rings following precontraction with carbachol. The trachea were cut into transverse rings containing two cartilage segments, and sutures were tied onto the cartilage on either side of the band of smooth muscle of each ring. The sutures were used to mount the individual rings in a 2.5-ml organ bath and to measure tension with an isometric force transducer. The water-jacketed organ baths maintained the preparation at 37° C. and were filled with Krebs Ringer solution aerated with 95% O$_2$ and 5% CO$_2$. The tracheal rings were equilibrated for 1 h following the application of 0.5 g resting tension. In some cases, equilibrated rings were then treated with the $\alpha_2$-antagonist rauwolscine (0.3 mM) and the $\beta_1$-antagonist atenolol (0.4 mM) prior to precontraction with carbachol (0.3 mM). Precontracted rings used as controls received treatments of saline only. Concentration-response curves were obtained by cumulative addition of drug to the organ bath, the concentration being increased only after the maximal relaxation to the preceding concentration was attained. After the final response was attained, isoproterenol (10 mM) was added to assess maximal response for each preparation.

For evaluation of α-adrenergic activity, male New Zealand white rabbits (2.5 kg) (Simunek Rabbitry, Vista, Calif.) were sacrificed by carbon dioxide inhalation and the thoracic aorta was quickly excised and placed in Krebs Ringer solution. The aorta was cut into 3-mm rings which were subsequently suspended on hooks in organ baths. The 2.5-ml water-jacketed baths were maintained at 37° C. and filled with Krebs Ringer solution aerated with 95% O$_2$ and 5% CO$_2$. The vascular rings were equilibrated for 1 h following the application of a resting tension of 4 g, during which time the buffer was changed at 15-min intervals. All rings were pretreated with propranolol (10 mM) 10 min prior to addition of test compounds. Concentration-response curves were obtained by cumulative addition of compound to the organ bath, the concentration being increased only after maximal response to the preceding concentration was attained. After the final response was attained for each test drug, norepinephrine (100 mM) was added to assess maximal contraction. Responses are expressed as a percent of the maximal contraction by norepinephrine.

In all experiments, tension was measured by isometric force transducers (52–9529, Harvard Apparatus, Natick, Mass.) coupled to an ink-writing recorder (Gould, Cleveland Ohio). The Krebs Ringer solution contained the following ingredients (mM): NaCl (118.1), NaHCO3 (25.0), D-glucose (11.1), KH$_2$PO$_4$ (1.2), KCl (4.8), MgSO$_4$ (1.2), CaCl$_2$ (2.5), pH=7.4.

Results in these assays are indicated below.

| Example # | $\beta_1$ (atria) | $\beta_2$ (trachea) | α (aorta) |
|---|---|---|---|
| 1 | 4.6 ± 0.7 | 4.7 ± 1.2 | 7500 ± 2840 |
| 2 | 3.4 ± 0.4 | 2.7 ± 0.5 | 15600 ± 8220 |
| 3 | 19 ± 5.4 | 21 ± 3.0 | 61300 ± 3820 |
| 4 | 1.1 ± 0.2 | 9.9 ± 1.3 | >100000 |
| 5 | 1.5 ± 0.4 | 8.2 ± 1.6 | 51800 ± 19200 |
| 6 | 14.9 ± 3.6 | 140 ± 35.3 | >10000 |
| 7 | 13.3 ± 1.0 | 245 ± 84.7 | 5500 ± 456 |
| 8 | 0.6 ± 0.3 | 4.6 ± 0.2 | 20900 ± 9850 |
| 9 | 2.9 ± 0.6 | 20 ± 3.4 | 1400 ± 82 |
| 10 | 4.8 ± 0.7 | 124 ± 13.6 | >10000 |
| 11 | 9.7 ± 2.0 | 16 ± 1.2 | 88300 ± 5660 |
| * | 1.4 ± 0.3 | — | 7830 ± 239 |

*1 (R)-(3,4-dihyroxyphenyl)-2-(1-methyl-4-methylsulfinylbutylamino) ethanol oxalate salt.

We claim:
1. A compound of the formula:

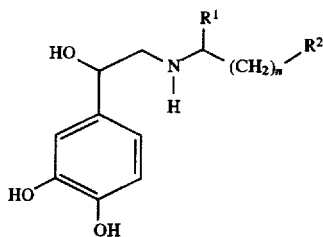

wherein:

$R^1$ is —H or lower alkyl of 1 to 3 carbon atoms;
$R^2$ is —$N_3$, —CN, —$OR^3$, or —$S(O)_pR^3$;
$R^3$ is lower alkyl of 1 to 3 carbon atoms;
p is zero, 1 or 2;
n is an integer from 1 to 5;
and pharmaceutically acceptable salts thereof.

2. A compound of claim 1 wherein $R^2$ is —$S(O)_pR^3$.
3. The compound of claim 2 where p is zero.
4. The compound of claim 3 where $R^1$ is —H, methyl or ethyl.
5. The compound of claim 4 where $R^3$ is —$CH_3$.
6. The compound of claim 5 where n is 2 or 3.
7. The compound of claim 2 wherein p is 1.
8. The compound of claim 2 selected from:

1-(R)-(3,4-dihydroxyphenyl)-2-(1-methyl-4-methylthiobutylamino)ethanol;

1-(R)-(3,4-dihydroxyphenyl)-2-(4-methylthiobutylamino)ethanol;

1-(R)-(3,4-dihydroxyphenyl)-2-(3-ethylthiopropylamino)ethanol;

1-(R)-(3,4-dihydroxyphenyl)-2-(3-methylsulfinylpropylamino)ethanol;

1-(R)-(3,4-dihydroxyphenyl)-2-(4-methylsulfinylbutylamino)ethanol; and pharmaceutically acceptable salts thereof.
9. The compound of claim 1 selected from:

1-(R)-(3,4-dihydroxyphenyl)-2-(3-methylthiopropylamino)ethanol; and pharmaceutically acceptable salts thereof.

10. The compound of claim 1 wherein $R^2$ is —CN.
11. The compound of claim 10 wherein n is 2 or 3.
12. The compound of claim 10 selected from:

1-(R)-(3,4-dihydroxyphenyl)-2-(3-cyanopropylamino)ethanol;

1-(R)-(3,4-dihydroxyphenyl)-2-(1-methyl-4-cyanobutylamino)ethanol; and pharmaceutically acceptable salts thereof.

13. The compound of claim 1 wherein $R^2$ is —$OR^3$.

14. The compound of claim 13 wherein n is 2 or 3.
15. The compound of claim 14 wherein $R^3$ is methyl.
16. The compound of claim 13 selected from:

1-(R)-(3,4-dihydroxyphenyl)-2-(3-methoxypropylamino)ethanol;

1-(R)-(3,4-dihydroxyphenyl)-2-(1-methyl-3-methoxypropylamino)ethanol;

1-(R)-(3,4-dihydroxyphenyl)-2-(1-methyl-4-methoxybutylamino)ethanol;

and pharmaceutically acceptable salts thereof.

17. A method of diagnosing and evaluating coronary artery disease in a mammal by eliciting in said mammal immediate cardiovascular responses similar to those cardiovascular responses elicited by aerobic activity which comprises:

a) administering an exercise simulating agent of formula I to said mammal by a drug delivery device; wherein the exercise simulating agent has formula:

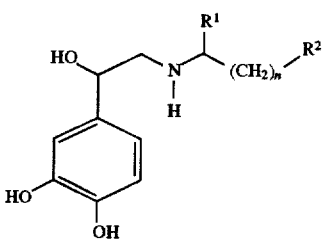

wherein:

$R^1$ is —H or lower alkyl of 1 to 3 carbon atoms;
$R^2$ is —$N_3$, —CN, —$OR^3$, or —$S(O)_pR^3$, wherein
$R^3$ is lower alkyl of 1 to 3 carbon atoms;
p is zero, 1 or 2;
n is an integer from 1 to 5;
and pharmaceutically acceptable salts thereof;

b) controlling infusion of said exercise simulating agent into the bloodstream of said mammal so that a predetermined range of cardiovascular responses of said mammal is obtained;

c) monitoring the range of responses of said mammal;

d) changing the rate of infusion of said exercise simulating agent as required to maintain said range of responses in said mammal; and e) evaluating said responses.

18. A method of claim 17 wherein $R^2$ is —$S(O)_pR^3$.
19. A method of claim 18 wherein p is zero.
20. A method of claim 18 wherein said exercise simulating agent is 1-(R)-(3,4-dihydroxyphenyl)-2-(3-methylthiopropylamino)ethanol and pharmaceutically acceptable salts thereof.

* * * * *

UNITED STATES PATENT AND TRADEMARK OFFICE
CERTIFICATE OF CORRECTION

PATENT NO. : 5,775,329
DATED : July 7, 1998
INVENTOR(S) : Ernest K. Metzner, et al.

It is certified that error appears in the above-identified patent and that said Letters Patent is hereby corrected as shown below:

Column 11, Line 54: delete "2(3" and insert --2-(3--

Column 12, Line 14: delete "2(1" and insert --2-(1--

Column 12, Line 42: delete "2(3" and insert --2-(3--

Column 13, Line 17: delete "2(1" and insert --2-(1--

Column 14, Line 16: delete "2(1" and insert --2-(1--

Column 14, Line 36: delete "(1methyl)" and insert --(1-methyl--

Column 15, Line 20: delete "ethylthioproylamino" and insert --ethylthiopropylamino--

Column 15, Line 31: delete "ethylthioproylamino" and insert --ethylthiopropylamino--

Column 15, Line 45: delete "methylthioproylamino" and insert --methylthiopropylamino--

Signed and Sealed this

Twenty-sixth Day of September, 2000

Attest:

Q. TODD DICKINSON

*Attesting Officer*   *Director of Patents and Trademarks*